United States Patent

Wong

[11] 4,407,807
[45] Oct. 4, 1983

[54] PYRIDYLPROPYL CYCLOALKANECARBOXYLATES: INSECT REPELLENTS

[75] Inventor: Rayman Y. Wong, Richmond, Calif.

[73] Assignee: Stauffer Chemical Company, Westport, Conn.

[21] Appl. No.: 332,568

[22] Filed: Dec. 21, 1981

Related U.S. Application Data

[63] Continuation-in-part of Ser. No. 223,515, Jan. 8, 1981, abandoned.

[51] Int. Cl.$^3$ .................... C07D 213/55; A01N 43/40
[52] U.S. Cl. ..................................... 424/263; 546/342
[58] Field of Search ......................... 546/342; 424/263

[56] References Cited

U.S. PATENT DOCUMENTS 4,093,622  6/1978  Henrick et al. .................... 546/342

OTHER PUBLICATIONS

Wright, Scientific American, vol. 233, No. 1, pp. 104–111, Jul. 1975.
Dethier et al., Journal of Economic Entomology, vol. 53, No. 1, pp. 134–136, 1960.

Primary Examiner—Alan L. Rotman
Attorney, Agent, or Firm—Joel G. Ackerman

[57] ABSTRACT

Compounds having the formula

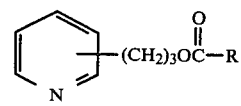

in which R is $C_3$–$C_5$ cycloalkyl, are insect repellents.

13 Claims, No Drawings

PYRIDYLPROPYL CYCLOALKANECARBOXYLATES: INSECT REPELLENTS

This application is a continuation-in-part of application Ser. No. 223,515, filed Jan. 8, 1981 now abandoned.

This invention relates to compounds having the formula

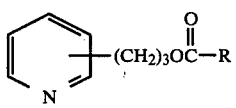

in which R is $C_3$–$C_5$ cycloalkyl. The side chain may be substituted on the pyridine ring at the 2-, 3-, or 4-position.

The compounds have utility as insect repellents, particularly for repelling flying insects from lighting and/or feeding.

The compounds of this type can be prepared by reaction of an appropriate pyridyl propanol with an appropriate acyl halide;

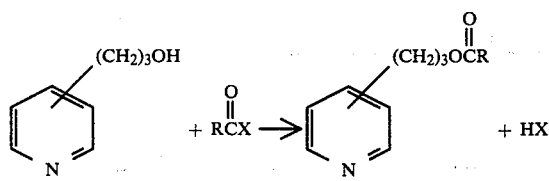

in which X is halogen, preferably chlorine, and R is as defined above.

The reaction is generally conducted at temperatures of about 0° C. to about 15° C., in the presence of a solvent such as methylene chloride, chloroform, other chlorinated hydrocarbon solvents, tetrahydrofuran or an ether, and a base, preferably an amine such as triethylamine or pyridine.

Compounds in which R is cyclopropyl are known; their preparation is illustrated by Example 15 of U.S. Pat. No. 4,093,622.

The following represent examples of the preparation of novel compounds in which R is cyclobutyl and cyclopentyl, respectively.

EXAMPLE 2

Preparation of 3-(3-pyridyl)-1-propyl cyclobutanoate (Compound 4 herein)

In a flask were mixed 5.0 grams (g.) (0.0364 mole) 3-(3-pyridyl)-1-propanol, 4.0 g. triethylamine and 50 milliliters (ml.) methylene chloride. The resulting solution was cooled to 0° C.; then 4.7 g. (0.04 mole) cyclobutane carboxylic acid chloride was added with stirring, at such a rate as to maintain the temperature at a maximum of about 15° C. A substantial amount of white solids precipitated, presumably the amine hydrochloride. On completion of the addition, the mixture was stirred at room temperature for 1 hour.

The resulting mixture was washed with water, aqueous sodium hydroxide, water, and saturated aqueous sodium chloride, and dried over sodium sufate. The dried product was filtered and the solvent was removed in vacuo, yielding 7.9 g. (99% of theoretical yield) of a rose colored oil, $nD^{30}$ 1.5040. The structure was confirmed by infrared (ir), nuclear magnetic resonance (nmr), and mass (ms) spectroscopy.

EXAMPLE 2

Preparation of 3-(3-pyridyl)-1-propyl cyclopentanoate (Compound 5 herein)

In a flask were mixed 12.7 g. (0.093 mole) 3-(3-pyridyl)-1-propanol, 7.4 g. pyridine and 120 ml. methylene chloride. The resulting solution was cooled to 0° C.; then 12.3 g. (0.093 mole) of cyclopentane carboxylic acid chloride was added, with stirring, at such a rate as to maintain the temperature at a maximum of about 15° C. When the addition was complete, the mixture was stirred for 1 hour at room temperature.

The resulting solution was washed with water, saturated aqueous sodium bicarbonate, water again, and saturated aqueous sodium chloride, and dried over sodium sulfate. The dried product was filtered and the solvent removed in vacuo. There was obtained 8.2 g. (38% of theoretical yield) of a clear yellow oil, $nD^{30}$ 1.5029. The structure was confirmed by ir, nmr, and ms.

The following Table I contains a list of representative compounds of this invention.

TABLE I

| Compound No. | R | Position on Pyridine Ring | $nD^{30}$ |
| --- | --- | --- | --- |
| 1 | cyclopropyl | 3- | 1.5075 |
| 2 | cyclopropyl | 4- | 1.5513 |
| 3 | cyclopropyl | 2- | 1.5034 |
| 4 | cyclobutyl | 3- | 1.5040 |
| 5 | cyclopentyl | 3- | 1.5029 |

The structures of the compounds in the foregoing Table I were confirmed by ir, nmr, and/or ms.

Insect Repellent Tests

Compounds described in the above Table I were tested for insect repellency by the following procedures:

Southern House Mosquitoes

A paper cup filled with pupae of the mosquito *Culex pipiens quinquefasciatus* (Say) was placed in a screened cage and the pupae allowed to emerge into adults. Sugar cubes were then saturated with 1.0 milliliter (ml.) of an acetone solution containing 0.1 wt. % of the test compound, and, for a control, with the same amount of acetone alone. After the cubes dried they were put into the screened cage. Repellency was determined by the number of mosquito adults lighting and feeding on the sugar cubes, with observations being made daily for 5 days after treatment. The number of days of complete repellency of mosquitoes from the sugar cubes was recorded.

Comparative tests were similarly conducted using the compound N,N-diethyl-m-toluamide, commercially manufactured and employed as an insect repellent, generally known by the generic name "deet". The results of the tests of deet and the compounds of Table I are shown in the following Table II. The numbers in each column represent the number of days of complete repellency observed using the specified concentration.

TABLE II

| (Southern House Mosquito) | |
|---|---|
| Compound | Days Repelled, 0.1 wt. % |
| 1 | 5 |
| 2 | 5 |
| 3 | 2 |
| 4 | 15 |
| deet | 1 |
| control | 0 |

Houseflies

The insect utilized for this test was the housefly, *Musca domestica* (L.). One hundred houseflies of mixed sexes were placed in test cages. In each cage was placed a sugar cube saturated with 1.0 ml of acetone containing 1 wt. % of the test compound. The cube was dried and weighed before being placed in the cage. Each cage also contained a water-saturated cotton plug, to provide moisture. The test cages were placed on a turntable and rotated at 6.0 revolutions per minute to keep the flies randomly distributed inside the cage. After 48 hours the flies in each cage were anesthetized with carbon dioxide. The sugar cubes were removed and reweighed and the percentage weight loss (due to consumption by the flies) recorded. A repellency ratio, calculated as the percent weight loss of the treated sugar cube divided by the percent weight loss of a control sugar cube treated with acetone only was calculated. The lower the repellency ratio, the greater the repellency of the test compound. The repellency ratios of the test compounds are shown in the following Table III. Values given for the repellency ratio represent an average of from one to three replications per compound.

TABLE III

| (Housefly) | |
|---|---|
| Compound | Repellency Ratio; Concentration, 1 wt. % |
| 1 | 0.58 |
| 2 | 0.48 |
| 3 | 0.47 |
| 4 | 0.59 |

Stable Fly; Yellow Fever Mosquito

Insects utilized for these tests were the stable fly, *Stomoxys calcitrans* and yellow fever mosquito, *Aedes aegypti*.

Pupae of these insects were placed in separate standard fly cages and allowed to emerge into adults. The mosquitoes were supplied with a sugar-water solution; the stable flies with water, sugar cubes, and casein. Tests on mosquitoes were performed at least 3 days after the adults emerged; those on stable flies, one day after emergence because of the short life span (4–5 days) of these flies without a blood meal.

Test compounds were weighed and dissolved in acetone. One milliliter (ml) of the test solution was pipetted onto a 9×9 cm. swatch of cotton stocking. The swatches were then allowed to dry for 1 hour.

A square opening 6×6 cm. was made in an upper corner of one side of each fly cage. A large, hard cardboard disk was placed over the opening so that it could be rotated to either cover or expose the opening as desired. One-half of the disc was left intact. In the remaining half, several 6×6 cm. square openings were cut. When the intact half of this disc was located over the opening in the fly cage, this opening was effectively sealed.

Swatches of treated stocking were placed over the square holes in the disc and held in place by metal frames attached to magnetic tape.

To initiate the test, the disc was rotated so that a treated swatch became located over the opening in the cage. The palm of the tester's hand was placed over a cardboard ring, 8 cm. in diameter and 1 cm. thick. The ring acted as a spacer and protected the hand from bites which could otherwise be inflicted by the insects. A breath of air was exhaled through tubing into the opening, so that insects could be attracted to the swatch by the warm, moist air and the tester's hand. The number of insects landing on the swatch was observed, and the number probing, recorded during a 1-minute exposure. Repellency was considered to occur when 5 or fewer insects probed the swatch during the exposure.

The compounds were tested at applications rates ranging from 0.1 mg/cm$^2$ of swatch downwards. The results of these tests on stable flies (SF) and yellow fever mosquitoes (YFM) are contained in Table IV.

TABLE IV

| (Stable Fly, Yellow Fever Mosquito) | | |
|---|---|---|
| | Repellent Concentration, mg/cm$^2$ | |
| Compound | SF | YFM |
| 1 | >0.1 | 0.1 |
| 2 | >0.1 | >0.1 |
| 3 | >0.1 | 0.1 |
| 4 | 0.1 | 0.1 |
| 5 | 0.1 | >0.1 |

The active compounds of this invention may be used as insect repellents in either diluted or undiluted form. When used in a diluted form, the compounds may be embodied in compositions containing relatively high or relatively low concentrations of the active compound. For example, the active compound can be incorporated into relatively high concentration compositions such as wet sprays or solutions in alcohol or other suitable solvents. Such compositions may contain, in addition to the active compound, adjuvants such as emulsifying agents, surface active agents, anti-oxidants and propellants which may be found normally in insect repellent preparations. The active compounds of this invention may be employed as the sole active component of such compositions or may be used in admixture with other compounds having a similar or different utility. For example, the compounds may be incorporated into creams, lotions, powders, suntan oil, insecticides and other preparations which may contain pesticidal or other useful substances, as well as into compositions of various types used for treating fabrics or articles of clothing to render them insect repellent. In general, compositions for repellent use may contain from 0.5 to up to 80 weight %, preferably from 2 to about 40 weight %, of the novel active compounds. High concentration formulations, containing up to 95% of the compounds, could also be utilized for low-volume spraying from the air.

Examples of typical formulations employing compounds of this invention are for instance,

EXAMPLE 1: EMULSIFIABLE CONCENTRATE

| Component | Weight % |
|---|---|
| Compound 1 | 53.6 |

EXAMPLE 2: LOTION

| Component | Weight % |
| --- | --- |
| Compound 2 | 10.7 |
| Lanolin | 4.8 |
| Mineral oil | 8.0 |
| Trihydroxyethylamine stearate | 1.8 |
| Glycosterin | 0.8 |
| Glycerine | 4.6 |
| Sodium benzoate | 1.0 |
| Water | 68.3 |
| Total | 100.0 |

EXAMPLE 3: ALCOHOL SOLUTION

| Component | Weight % |
| --- | --- |
| Compound 3 | 53.6 |
| Isopropanol | 46.4 |
| Total | 100.0 |

EXAMPLE 4: ALCOHOL SOLUTIONS

| Component | Weight % |
| --- | --- |
| Compound 4 | 80.0 |
| Ethanol | 20.0 |
| Total | 100.0 |

EXAMPLE 5: WETTABLE POWDER

| Component | Weight % |
| --- | --- |
| Compound 5 | 26.9 |
| Hydrated calcium silicate | 62.1 |
| Sodium lignosulfonate | 5.0 |
| Orzan A (mixture of ammonium lignosulfonate and wood sugars) | 5.0 |
| Wetting agent | 1.0 |
| Total | 100.0 |

What is claimed is:

1. A compound having the formula

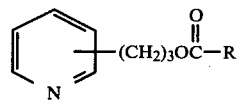

in which R is cyclobutyl.

2. A compound according to claim 1 in which the side chain is substituted on the pyridine ring at the 3-position.

3. An insect repellent composition containing an insect-repelling effective amount of a compound according to claim 1 and an inert diluent or carrier.

4. A method of repelling but not killing insects selected from mosquitoes, houseflies or stable flies from a locus to be protected therefrom, comprising applying to said locus an effective insect repelling but non-lethal amount to said insects of a compound having the formula

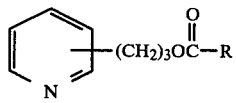

in which R is $C_3$–$C_5$ cycloalkyl.

5. A method according to claim 4 in which the compound is applied in an amount effective to repel mosquitoes.

6. A method according to claim 4 in which the compound is applied in an amount effective to repel houseflies.

7. A method according to claim 4 in which the compound is applied in an amount effective to repel stable flies.

8. A method according to claim 4 in which R is cyclopropyl.

9. A method according to claim 8 in which the side chain is substituted on the pyridine ring at the 2-position.

10. A method according to claim 8 in which the side chain is substituted on the pyridine ring at the 3-position.

11. A method according to claim 8 in which the side chain is substituted on the pyridine ring at the 4-position.

12. A method according to claim 4 in which R is cyclobutyl.

13. A method according to claim 4 in which R is cyclopentyl.

* * * * *